United States Patent [19]

Gericke et al.

[11] Patent Number: 5,238,937

[45] Date of Patent: Aug. 24, 1993

[54] PYRIDAZINY OR OXODIHYDROPYRIDAZINYL CHROMAN DERIVATIVES

[75] Inventors: Rolf Gericke, Seeheim; Manfred Baumgarth, Darmstadt; Ingeborg Lues, Darmstadt; Jürgen Harting, Darmstadt; Rolf Bergmann, Reichelsheim, all of Fed. Rep. of Germany

[73] Assignee: Merck Patent Gesellschaft, Darmstadt, Fed. Rep. of Germany

[21] Appl. No.: 802,093

[22] Filed: Dec. 4, 1991

[30] Foreign Application Priority Data

Dec. 5, 1990 [DE] Fed. Rep. of Germany ....... 4038752

[51] Int. Cl.$^5$ .................... A61K 31/50; C07D 237/04; C07D 237/06
[52] U.S. Cl. .................... 514/253; 514/252; 514/255; 514/256; 514/269; 544/230; 544/238; 544/298; 544/318; 544/319; 544/322; 544/336; 546/269
[58] Field of Search ............... 544/230, 238; 514/252, 514/253

[56] References Cited

U.S. PATENT DOCUMENTS 5,013,853  5/1991  Gericke et al. ................ 544/238

Primary Examiner—Mukund J. Shah
Assistant Examiner—Y. N. Gupta
Attorney, Agent, or Firm—Millen, White, Zelano & Branigan

[57] ABSTRACT

The invention relates to novel chroman derivatives of the formula I

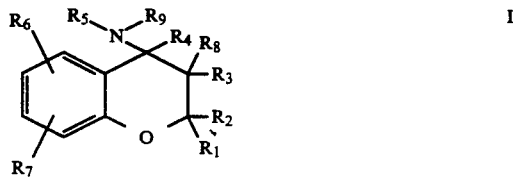

in which $R^1$, $R^2$, $R^3$, $R^4$, $R^5$, $R^6$, $R^7$, $R^8$ and $R^9$ have the meanings given in [Patent claim 1], and which, like their salts, show effects on the cardiovascular system and can be used for the treatment or prophylaxis of cardiac insufficiency, angina pectoris, high blood pressure, incontinence and alopecia.

5 Claims, No Drawings

PYRIDAZINY OR OXODIHYDROPYRIDAZINYL CHROMAN DERIVATIVES

SUMMARY OF THE INVENTION the invention relates to novel chroman derivatives of the formula I

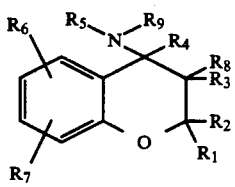

in which
$R^1$ is A,
$R^2$, $R^8$ and $R^9$ are each H or A,
$R^1$ and $R^2$ together are also alkylene having 3–6 C atoms,
$R^3$ is H, OH, OA or $OR^{10}$,
$R^4$ is H,
$R^3$ and $R^4$ together are also a bond,
$R^5$ is a pyridyl, pyridazinyl, pyrimidinyl, pyrazinyl, oxodihydropyridyl, oxodihydropyridazinyl, oxodihydropyrimidinyl or oxodihydropyrazinyl radical which is unsubsituted, monosubstituted or disubstitued by A, F, Cl, Br, I, OH, OA, $OR^{10}$, SH, $NO_2$, $NH_2$, $R^{10}NH$, HOOC and/or AOOC,
$R^6$ and $R^7$ are each H, A, HO, AO, CHO, ACO, ACS, HOOC, AOOC, AO—CS, ACOO, A—CS—O, HO—$C_nH_{2n}$, HS—$C_nH_{2n}$, $NO_2$, $NH_2$, NHA, $NA_2$, CN, F, Cl, Br, I, $CF_3$, ASO, $ASO_2$, AO—SO, AO—$SO_2$, $R^{10}NH$, AO—CO—NH, $H_2NSO$, HANSO, $A_2NSO$, $H_2NSO_2$, $HANSO_2$, $A_2NSO_2$, $H_2NCO$, HANCO, $A_2NCO$, $H_2HCS$, HANCS, $A_2NCS$, ASONH, $ASO_2NH$, AOSONH, $AOSO_2NH$, ACO—$C_n$—$H_{2n}$, nitro—$C_nH_{2n}$, Cyano$C_nH_{2n}$, A—C(=NOH) or A—C(=$NNH_2$),
A is alkyl having 1–6 C atoms,
$R^{10}$ is alkanoyl having 1–8 C atoms or aroyl having 7–11 atoms, and
n is 1, 2, 3, 4, 5 or 6
and their salts.

The invention was based on the object of finding novel compounds having useful properties, in particular those which can be used for the preparation of medicaments.

It has been found that the compounds of the formula I and their physiologically acceptable salts possess, combined with good tolerability, useful pharmacological properties. Thus, they show effects on the cardiovascular system, it usually being possible to observe a selective effect on the coronary system at lower doses and a hypotensive effect at higher doses. In the coronary system, for example, decreases in resistance and increases in flow occur, the influence on the heart rate remaining low. Furthermore, the compounds show a relaxant effect on various smooth muscle organs (gastrointestinal tract, respiratory system and uterus). The effects of the compounds can be determined with the aid of methods which are known per se, as are given, for example, in EP-A-76,075, EP-A-168,619, EP-A-173,848 or AU-A-45,547/85 (Derwent Farmdoc No. 86081769) and by K. S. Meesmann et. al., Arzneimittelforschung 25 (11), 1975, 1770–1776. Suitable experimental animals are, for example, mice, rats, guinea pigs, dogs, cats, apes or pigs.

The compounds can therefore be used as active medicament compounds in human and veterinary medicine. In addition, they can be used as intermediates for the preparation of further active medicament compounds.

In the formulae given, A is a preferably unbranched alkyl group having 1–6, preferably 1–4, in particular 1, 2 or 3 C atoms, in detail preferably methyl, in addition preferably ethyl, propyl, isopropyl, butyl, isobutyl, and furthermore preferably sec.-butyl, tert.-butyl, pentyl, isopentyl (3-methylbutyl), hexyl or isohexyl (4-methylpentyl).

If $R^1$ and $R^2$ together are alkylene, the alkylene group is preferably unbranched, in detail preferably —($CH_2$)$_m$—, where m is 3, 4, 5 or 6.

$R^{10}$ is preferably alkanoyl having 1–6, in particular 1, 2, 3 or 4 C atoms, in detail preferably formyl or acetyl, furthermore preferably propionyl, butyryl, isobutyryl, pentanoyl or hexanoyl, and in addition preferably benzoyl, o-, m- or p-toluyl, 1- or 2-naphthoyl. AOSONH, $AOSO_2NH$, ACO—$C_n$—$H_{2n}$, nitro—$C_nH_{2n}$, Cyano $R^1$ and $R^2$ are preferably each alkyl, in particular each methyl or ethyl, preferably each methyl.

If $R^4$ is H, $R^3$ is preferably OH, and in addition preferably O—$COCH_3$. In the same way, $R^3$ and $R^4$ together can also be an additional bond.

$R^5$ is preferably unsubstituted 2-oxo-1,2-dihydro-1- or -3-pyridyl, 4-oxo-1,4-dihydro-3-pyridyl or else substituted 1,2-dihydro-2-oxo-4-pyridyl, particularly preferably-methyl-1,2-dihydro-2-oxo-4-pyridyl, furthermore preferably unsubstituted or substituted 6-oxo-1,6-dihydro-3-pyridazinyl, particularly preferably 6-oxo-1,6-dihydro-3-pyridazinyl substituted in the 1-position by methyl, ethyl, isopropyl or benzyl. $R^5$ can furthermore be 2-, 3- or 4-pyridyl, 3- or 4-pyridazinyl, 2-, 4- or 5-pyrimidinyl, 2-pyrazinyl, oxo-1,2-, oxo-3,4- or oxo-4,5-dihydro-pyrimidinyl or oxo-1,2-dihydro-pyrazinyl, each of which can be unsubstituted or mono- or disubstituted, substituents such as alkyl radicals having 1–6 C atoms, especially methyl, ethyl or isopropyl, fluorine, bromine, chlorine, iodine, hydroxyl, alkoxy, in particular methoxy or ethoxy, amino, mercapto or nitro radicals being particularly preferred.

Radicals of the type $R^5$ which contain an oxo group adjacent to a ring N atom may also exist in the tautomeric lactam. In the same way, the heteroaromatic radicals $R^5$ with mercapto groups adjacent to the ring N atom can also exist in the tautomeric thiolactam form, and vice versa.

$R^6$ and $R^7$ are preferably:
A: methy, and in addition ethyl;
AO: methoxy, and in addition ethoxy;
ACO: acetyl, and in addition propionyl;
ACS: thioacetyl, and in addition thiopropionyl;
AOOC: methoxycarbonyl, and in addition ethoxycarbonyl;
AO—CS: methoxy-thiocarbonyl, and in addition ethoxythiocarbonyl;
ACOO: acetoxy, and in addition propionoxy;
ACSO: thio(no)acetoxy, and in addition thio(no)propionoxy;
HO—$C_nH_{2n}$: hydroxymethyl or 1- or 2-hydroxyethy;
HS—$C_nH_{2n}$: mercaptomethyl or 1- or 2-mercaptoethyl;
NHA: methylamino, and in addition ethylamino;
$NA_2$: dimethylamino, and in addition diethylamino;
ASO: methylsulfinyl, and in addition ethylsulfinyl;
$ASO_2$: methylsulfonyl, and in addition ethylsulfonyl;

AO—SO: methoxy-sulfinyl, and in addition ethoxysulfinyl;

AO—SO$_2$: methoxy-sulfonyl, and in additon ethoxysulfonyl;

R$^{10}$—NH: acetamido, and in addition formamido, propionamido or benzamido;

AO—CO—NH methoxycarbonylamino, and in addition ethoxycarbonylamino;

HANSO: methylaminosulfinyl, and in addition ethylaminosulfinyl;

A$_2$NSO: dimethylaminosulfinyl, and in addition dimethylaminosulfinyl;

HANSO$_2$: methylaminosulfinyl, and in addition ethylaminosulfonyl;

A$_2$NSO$_2$: dimethylaminosulfonyl, and in addition diethylaminosulfonyl;

HANCO: N-methylcarbamoyl, and in addition N-ethylcarbamoyl;

A$_2$NCO: N,N-dimethylcarbamoyl, and in addition N,N-diethylcarbamoyl;

HANCS: N-methylthiocarbamoyl, and in addition N-ethylrhiocarbamoyl;

A$_2$NCS: N,N-dimethylthiocarbamoyl, and in addition N,N-diethylthiocarbamoyl;

ASONH: methylsulfinylamino, and in addition ethylsulfinylamino;

ASO$_2$NH: methylsulfonylamino, and in addition ethylsulfonylamino;

AOSONH: methoxysulfinylamino, and in addition ethoxysulfinylamino;

AOSO$_2$NH: methoxysulfonylamino, and in addition ethoxysulfonylamino;

ACO—C$_n$H$_{2n}$: 2-oxopropyl, 2-oxobutyl, 3-oxobutyl, 3-oxopentyl;

Nitro—C$_n$H$_{2n}$: nitromethyl, 1- or 2-nitroethyl;

Cyano—C$_n$H$_{2n}$: cyanomethyl, 1- or 2-cyanoethyl;

A—C(=NOH): 1-oximinoethyl, and in addition 1-oximinopropyl;

A—C(=NNH$_2$): 1-hydrazonoethyl, and in addition 1-hydrazonopropyl.

The variable "n" can assume values from 1-6, hydrazonpropyl.

The radicals R$^5$ and R$^7$ are preferably in the 6- and 7-position of the chroman system. However, they may also be in the 5- and 6-, 5- and 7-, 5- and 8-, 6- and 8- and 7- and 8-position.

One of the radicals R$^6$ and R$^7$ is preferably H, whereas the other is different from H. This other radical is preferably in the 6-position, but also in the 5-, 7- or 8-position, and is preferably CN or NO$_2$, in addition preferably CHO, ACO (in particular acetyl), AOOC (in particular methoxycarbonyl or ethoxycarbonyl), ACOO (in particular acetoxy), and furthermore preferably F, Cl, Br, I, CF$_3$, H$_2$NCO, H$_2$NCS or NH$_2$.

The radical Rs is preferably H, and furthermore preferably methyl or ethyl.

Accordingly, the invention in particular relates to those compounds of the formula I in which at least one of the radicals mentioned has one of the previously mentioned preferred meanings. Some preferred groups of compounds can be expressed by the formulae Ia to Ij below, which correspond to the formula I and in which the radicals not designated in more detail have the meaning indicated in the formula I, in which however
in IA R$^1$ and R$^2$ are each A;
in Ib
R$^1$ and R$^2$ are each CH$_3$;
in Ic
R$^1$ and R$^2$ together are alkylene having 3-6 C atoms;
in Id
R$^5$ is a pyridyl, pyridazinyl, pyrimidinyl or pyrazinyl radical which is unsubstituted or substituted by an OH group or an oxodihydropyridyl or oxodihydropyridazinyl radical which is substituted by A;
in Ie
R$^5$ is a 6-oxo-1,6-dihydro-3-pyridazinyl radical which is substituted in the 1-position by methyl, ethyl, isopropyl or benzyl;
in If
R$^5$ is a 2-oxo-1,2-dihydro-1, -2- -3- or -4-pyridyl radical or a 4-oxo-1,4-dihydro-3-pyridyl radical;
in Ig
R$^5$ is a 1-methyl-2-oxo-1,2-dihydro-4-pyridyl radical;
in Ih
R$^1$ and R$^2$ are each CH$_3$ together are —(CH$_2$)$_4$—or —(CH$_2$)$_5$—;
R$^5$ is a pyridyl, pyridazinyl, pyrimidinyl or pyrazinyl radical which is unsubstituted or substituted by an OH group or an oxodihydropyridyl or oxodihydropyridazinyl radical which is substituted by A, and
R$^8$ and R$^9$ are each H or CH$_3$.
in Ii
R$^1$ and R$^2$ are each CH$_3$;
R$^5$ is a 1-methyl-, 1-ethyl-, 1-isopropyl- or 1-benzyl-6-oxo-1,6-dihydro-3-pyridazinyl radical, and
R$^9$ is H or methyl,
in Ij
R$^1$ and R$^2$ are each CH$_3$;
R$^5$ is 2-oxo-1,2-dihydro-1-, -2-, -3- or -4-pyridyl, 4-oxo-1,4-dihydro-3-pyridyl or 1-methyl-2-oxo-1,2-dihydro-4-pyridyl, and R$^9$ is H or methyl.

Compounds of the formulaeI' and Ia' to Ij' are furthermore preferred which correspond to the formulae I and Ia to Ij, but in which in each case additionally R$^3$ is H, OH, OCHO or OCOCH$_3$ and R is H, in particular those compounds of the formulae I' and Ia' to Ij' in which in each case additionally R$^3$ is OH and R$^4$ is H.

Compounds of the formulae I" and Ia" to Ij" are furthermore preferred which correspond to the formulae I and Ia to Ij, but in which in each case R$^3$ and R$^4$ together are additionally a bond.

Compounds of the formulae I, I', I", Ia to Ij, Ia' to Ij' and Ia" to Ij" are in addition preferred, in which in each case additionally (a)
R$^6$ is different from H and
R$^7$ is H;
(b)
R$^6$ is different from H and is in the 6-position and
R$^7$ is H;
(c)
R$^6$ is NO$_2$, CN, CHO, ACO, HOOC, AOOC, ACOO, F, Cl, Br, I, CF$_3$, H$_2$NCO, H$_2$NCS or NH$_2$ and R$^7$ is H;
(d)
R$^6$ is NO$_2$, CH, CHO, ACO, HOOC, AOOC, ACOO, F, Cl, Br, I, CF$_3$, H$_2$NCO, H$_2$NCS or NH$_2$ and is in the 6-position and
R$^7$ is H;
(e)
R$^6$ is NO$_2$, CH, CHO, CH$_3$CO, CH$_3$OOC, C$_2$H$_5$OOC or CH$_3$COO and
R$^7$ is H;
(f)

$R^6$ is NO$_2$, CH, CHO, CH$_3$CO, CH$_3$OOC, C$_2$H$_5$OOC or CH$_3$COO and is in the 6-position and
$R^7$ is H;

(g)
$R^6$ is NO$_2$ or CN and
$R^7$ is H;

(h)
$R^6$ is NO$_2$ or CN and is in the 6-position and
$R^7$ is H;

(i)
$R^6$ is CN and
$R^7$ is H;

(j)
$R^6$ is CN and is in the 6-position and
$R^7$ is H.

Compounds of the formulae I, I', I'', Ia to Ij, Ia' and Ij', Ia'' to Ij'' and the remaining groups of compounds previously indicated as preferred are particularly preferred, in which $R^8$ is additionally CH$_3$.

Otherwise, the radicals $R^1$ to $R^{10}$ and A above and below have the meanings given in formula I, if not expressly stated otherwise.

The invention in addition relates to a process for the preparation of chroman derivatives of the formula I, characterized in that a chroman of the formula II

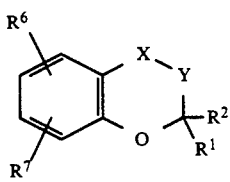

II in which

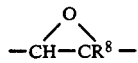

or —CHe—CR$^3$R$^8$—and E is Cl, Br, I or a reactively esterified OH group and $R^1$, $R^2$, $R^3$, $R^6$, $R^7$ and $R^8$ have the meanings given in formula I is reacted with a compound of the formula III $R^5$—NH—$R^9$ III in which $R^5$ and $R^9$ have the meanings indicated in formula I, or with one of its reactive derivatives and/or in that a compound of the formula I, in which $R^3$ is OH and $R^4$ is H, is dehydrated and/or in that one or more of the radicals $R^3$, $R^{5l}$, $R^6$ and/or $R^7$ are converted into other radicals $R^3$, $R^5$, $R^6$, and/or $R^7$ in a compound of the formula I and/or in that a basic compound of the formula I is converted into one of its acid addition salts by treating with an acid.

The compounds of the formula I are otherwise prepared by methods which are known per se, as are described in the literature (for example in the standard works such as Houben-Weyl, Methoden der organischen Chemie (Methods of Organic Chemistry), Georg-Thieme Verlag, Stuttgart; Organic Reactions, John Wiley & Sons, Inc., New York; and in the abovementioned patent applications), in particular under reaction conditions which are known and suitable for the reactions mentioned. In this case, use can also be made of variants which are known per se but which are not mentioned in more detail here.

The starting materials may also be formed, if desired, in situ in such a way that they are not isolated from the reaction mixture, but immediately reacted further to give the compounds of the formula I.

Preferably, the compounds of the formula I are prepared by reacting compounds of the formula II with compounds of the formula III, preferably in the presence of an inert solvent at temperatures between about 0° and 150°.

Starting materials of the formula II with X—Y=

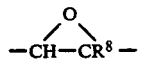

(3,4-epoxychromans) are preferred.

The starting materials II and III are usually known (compare, for example, DE-OS 3,726,261). If they are not known, they can be prepared by methods which are known per se. Thus, the starting materials of the formula

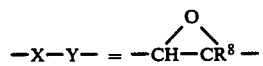

are obtainable by reacting 2-hydroxyacetophenones of the formula 2—HO—R$^6$R$^7$C$_6$H$_2$—COCH$_3$ with ketones of the formula R$^1$—CO—R$^2$ to give corresponding 4-chromanone of the formula IVa

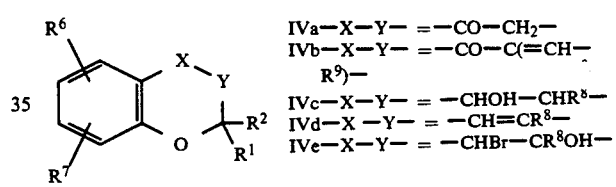

if desired condensing with aldehydes of the formula A—CHO (A=alkyl having 1-6 C atoms) to give 3-alkylidene-4-chromanones of the formula IVb, reducing, for example with NaBH$_4$, to give chromanols of the formula IVc, dehydrating, for example with p-toluenesulfonic acid, to give chromenes of the formula IVd and oxidising, for example with 3-chloroperbenzoic acid. The last-mentioned oxidation can also be carried out in a number of steps. Thus, for example, the bromohydrins of the formula IVe can initially be prepared using N-bromosuccinimide in aqueous solution and HBr can subsequently be eliminated from these using a base, for example sodium hydroxide solution.

The chromenes of the formula IVd can also be obtained by condensation of salicylaldehydes of the formula 2—HO—R$^6$R$^7$C$_6$H$_2$—CHO with ketones of the formula R$^1$—CO—CH$_2$—R$^8$ to give hydroxyketones of the formula 2—HO—R$^6$R$^7$C$_6$H$_2$—CH=CH$^8$—CO—R$^1$, reaction with organolithium compounds of the formula R$^2$—Li and subsequent hydrolysis to give diols of the formula 2—HO—R$^6$R$^7$C$_6$H$_2$—CH=CR$^8$—CR$^1$R$^2$—OH, and cyclisation with elimination of water.

In compounds of the formula II (—X—Y=—CHE—CR$^3$R$^8$—), possible "reactively esterified OH groups" are in particular esters with alkylsulfonic acids (in which the alkyl group contains 1-6 C atoms) or with arylsulfonic acids (in which the aryl group contains 6-10 C atoms). These compounds are obtainable from the 4-chromanols of the formula IVc by reacting with an inorganic acid halide such as PCl$_3$, PBr$_3$, SOCl$_2$ or SOBr$_2$ or with a sulfonyl chloride such as methanesulfonyl or p-toluenesulfonyl chloride.

Reactive derivatives of III which are suitable are the corresponding salts, for example the Na or K salts, which can also be formed in situ.

It is expedient to work in the presence of a base. Suitable bases are, for example, hydroxides, carbonates, alkoxides, hydrides and also amides of alkali metals or alkaline earth metals, such as NaOH, KOH, Ca(OH)$_2$, Na$_2$CO$_3$, K$_2$CO$_3$, Na methoxide or K methoxide, Na ethoxide or K ethoxide or Na tert.-butoxide or K tert.-butoxide, butoxide, NaH, KH, CaH$_2$, NaNH$_2$, KNH$_2$, and in addition organic bases such as triethylamine or pyridine, which can also be used in excess and then at the same time serve as solvent.

Suitable inert solvents are, in particular, alcohols such as methanol, ethanol, isopropanol, n-butanol or tert.-butanol; ethers such as diethyl ether, diisopropyl ether, tetrahydrofuran or dioxane; glycol ethers such as ethylene glycol monomethyl ether or ethylene glycol monoethyl ether (methyl glycol or ethyl glycol), ethylene glycol dimethyl ether (diglyme); ketones such as acetone or butanone; nitriles such as acetonitrile; nitro compounds such as nitromethane or nitrobenzene; esters such as ethyl acetate; amides such as dimethylformamide (DMF), dimethylacotamide or hexamethylphosphoramide; sulfoxides such as dimethyl sulfoxide (DMSO); chlorinated hydrocarbons such as dichloromethane, chloroform, trichloroethylene, 1,2-dichloroethane or carbon tetrachloride; hydrocarbons such as benzene, toluene or xylene. Mixtures of these solvents with one another are furthermore suitable.

The epoxide II

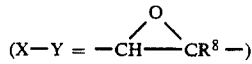

can also be prepared in situ, for example by the action of a base on the corresponding bromohydrin IVe.

A particularly preferred procedure consists in using an alcohol (for example ethanol) as a solvent and adding an organic base (for example pyridine), the reaction mixture expediently being boiled for about 0.5 to 20 hours.

A compound of the formula I in which R$^3$=OH and R$^4$=H can be converted into a compound of the formula I in which R$^3$ and R$^4$ together are a bond by treating with a dehydrating agent. This is carried out, for example by the action of one of the bases mentioned, for example NaH, in one of the solvents mentioned, for example DMSO, at temperatures between 0° and 150°.

Furthermore, one or more of the radicals R$^3$, R$^5$, R$^6$ and/or R$^7$ can be converted into other radicals R$^3$, R$^5$, R$^6$ and/or R$^7$ in a compound of the formula I.

For example, it is possible to replace an H atom by a halogen atom by means of a halogenation or by a nitro group by means of a nitration and/or to reduce a nitro group to an amino group and/or to alkylate or acylate an amino or hydroxyl group and/or to convert a cyano group (for example with HCl in water/methanol at 20°-100°) into a carboxyl group or (for example with Raney nickel in water/acetic acid/pyridine in the presence of sodium phosphate) into a formyl group or (for example with KOH in tert.-butanol) into a carbamoyl group or (for example with H$_2$S in pyridine/triethylamine) into a thiocarbamoyl group and/or to convert a —CO—NH—group, for example with P$_2$S$_5$ or with Lawesson reagent in toluene) into a —CS—NH—or —C(SH)=N—group.

Nitration is carried out under customary conditions, for example using a mixture of concentrated HNO$_3$ and concentrationed H$_2$SO$_4$ at temperatures between 0° and 30°. If at least one of the substituents R$^6$ and R$^7$ is an electronegative group such as CN or NO$_2$, the nitration predominantly takes place at the radical R$^5$; otherwise mixtures are usually obtained in which the nitro groups are on the radical R° or on the chroman ring.

This applies analogously to the halogenation which can be carried out, for example, using elemental chlorine or bromine in one of the customary inert solvents at temperatures between about 0° and 30°.

A primary or secondary amino group and/or an OH group can be converted into the corresponding secondary or tertiary amino group and/or alkoxy group by treating with alkylating agents. Suitable alkylating agents are, for example, compounds of the formulae A—Cl, A—Br or A—I or corresponding sulfuric acid or sulfonic acid esters, such as methyl chloride, bromide or iodide, dimethyl sulfate or methyl p-toluenesulfonate. In addition, for example, one or two methyl groups can be introduced with formaldehyde in the presence of formic acid. The alkylation is preferably carried out in the presence or absence of one of the inert solvents mentioned, for example DMF, at temperatures between about 0° and about 120°, in which case a catalyst can also be present, preferably a base such as potassium tert.-butoxide or NaH.

Suitable acylating agents for the acylation of amino or hydroxyl groups are preferably the halides (for example chlorides or bromides) or anhydrides of carboxylic acids, for example acetic anhydride, propionyl chloride, isobutyryl bromide, formic acid/acetic anhydride and benzoyl chloride The addition of a base such as pyridine or triethylamine during the acylation is possible The acylation is preferably carried out in the presence or absence of an inert solvent, for example a hydrocarbon such as toluene, a nitrile such as acetonitrile, an amide such as DMF or an excess of a tertiary base such as pyridine or triethylamine, at temperatures between about 0° and about 160°, preferably between 20° and 120°. Formulation is also carried out using formic acid in the presence of pyridine A base of the formula I can be converted into the respective acid addition salt using an acid. Acids which give physiologically acceptable salts are particularly suitable for this reaction Thus, inorganic acids can be used, for example sulfuric acid, nitric acid, hydrohalic acids such as hydrochloric acid or hydrobromic acid, phosphoric acids such as orthophosphoric acid, sulfamic acid, and in addition organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and -disulfonic acids, and laurylsulfuric acid. Salts with physiologically unacceptable acids, for example picrates, can be used for purifying the compounds of the formula I.

The compounds of the formula I may possess one or more chiral centers. They can therefore be obtained during their preparation as racemates or also, if optically active starting materials are used, in optically active form. If the compounds have two or more chiral centers, they may be obtained during synthesis as mixtures of racemates from which the individual racemates can be isolated in pure form, for example by recrystallising from inert solvents. Thus, for example, compounds of the formula I in which $R^1=R^2$, $R^3=OH$ and $R^4=H$ have two chiral centers; during preparation by reaction of II with III, however, very predominantly only one racemate having the trans-position of the substituents $R^3=OH$ and $R^5R^9N$ is formed. Racemates obtained can, if desired, be separated mechanically, chemically or biochemically into their enantiomers by methods known per se. Thus, diastereomers can be formed from the racemate by reaction with an optically active resolving agent. Suitable resolving agents for basic compounds of the formula I are, for example, optically active acids, such as the D and L-forms of tartaric acid, dibenzoyltartaric acid, diacetyltartaric acid, camphanic acid, camphorsulfonic acids, mandelic acid, malic acid or lactic acid. Carbinols (I, $R^3=OH$) can in addition be esterified and then resolved with the aid of chiral acylating reagents, for example the acids mentioned, in particular (+)- or (−)-camphanic acid or (+)- or (−)-camphor-10-sulphonic acid, or with D- or L-methylbenzyl isocyanate (cf. EP-Al-120,428). The different forms of the diastereomers can be separated in a manner known per se, for example by fractional crystallisation, and the enantiomers of the formula I can be liberated in a manner known per se from the diastereomers. Resolution of enantiomers is in addition carried out by chromatography on optically active support materials.

The compounds of the formula I and their physiologically acceptable salts can be used for the production of pharmaceutical preparations, in particular in non-chemical ways. In this connection, they can be brought into a suitable form for administration together with at least one solid, liquid and/or semi-liquid excipient or auxiliary and, if desired, in combination with one or more further active compound(s).

The invention in addition relates to agents, in particular pharmaceutical preparations, containing at least one compound of the formula I and/or one of its physiologically acceptable salts.

These preparations can be used as medicaments in human or veterinary medicine Suitable excipients are organic or inorganic substances which are suitable for external; (for example oral), parenteral or topical administration and which do not react with the novel compounds, for example water, vegetable oils, benzyl alcohols, polyethylene glycols, glycerol triacetate, gelatin, carbohydrates such as lactose or starch, magnesium stearate, talc, lanolin or petroleum jelly. Tablets, coated tablets, capsules, syrups, elixirs or drops are used in particular for oral administration, suppositories are used in particular for rectal administration, solutions, preferably oily or aqueous solutions, and in addition suspensions, emulsions or implants are used in particular for parenteral administration, and ointments, creams, pastes, lotions, gels, sprays, foams, aerosols, solutions (for example solutions in alcohols such as ethanol or isopropanol, acetonitrile, DMF, dimethylacetamide, 1,2-propanediol or their mixtures with each other and/or with water) or powders are used in particular for topical application. The novel compounds can also be lyophilised and the lyophilisates obtained used, for example, for the production of injection preparations. Liposomal preparations are in particular also suitable for topical application. The preparations mentioned can be sterilised and/or can contain auxiliaries such as lubricants, preservatives, stabilisers and/or wetting agents, emulsifiers, salts for influencing the osmotic pressure, buffer substances, colourants and flavourings and/or aromatisers. They can, if desired, also contain one or more further active compounds, for example one or more vitamins.

The compounds of the formula I and their physiologically acceptable salts can be administered to humans or animals, in particular mammals such as apes, dogs, cats, rats or mice and can be used in the therapy of disorders of the human or animal body, in particular in the therapy and/or prophylaxis of disturbances of the cardiovascular system, in particular decompensated cardiac insufficiency, angina pectoris, arrhythmia, peripheral or cerebral vessel disorders, and disease conditions which are connected with high blood pressure, and in addition disorders which are connected with changes in the nonvascular musculature, for example asthma or urinary incontinence. All of the compounds above have all of the utilities disclosed to at least a finite degree.

In this connection, the substances according to the invention are usually administered analogously to known antianginals or hypotensives, for example nicorandil or cromakalim, preferably in doses between about 0.01 and 5 mg, in particular between 0.02 and 0.5 mg per dose unit. The daily dose is preferably between about 0.0001 and 0.1, in particular between 0.0003 and 0.01 mg/kg of body weight. The specific dose for each particular patient depends, however, on a variety of factors, for example on the efficacy of the specific compound employed, on the age, body weight, the general state of health, sex, on the food, on the time and route of administration, on the excretion rate, medicament combination and severity of the particular disease to which the therapy applies. Oral administration is preferred.

The compounds of the formula I and their salts are in addition suitable, in particular on topical application, for the treatment of alopecia areata. For this purpose, in particular, pharmaceutical preparations are used which are suitable for the topical treatment of the scalp and which are mentioned above. They contain about 0.005 to 10, preferably 0.5 to 3, % by weight of at least one compound of the formula I and/or at least one of its salts. Otherwise, these compounds can be used against alopecia in analogy to the statements in WO 88/00822.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of Germany P 40 38 752.6, filed Dec. 5, 1990, are hereby incorporated by reference.

EXAMPLES

In the following examples, "customary working up'"means that the reaction mixture is treated with water and extracted using an organic solvent such as ethyl acetate, the organic phase is separated off and dried over sodium sulfate, and the residue is purified by column chromatography and/or crystallization.

EXAMPLE 1

2.0 g of 2,2-dimethyl-3,4-epoxy-6-cyanochroman ("IIa") are added to a mixture of 1.2 g of 3-amino-1-methyl-1,6-dihydropyridazin-6-one and 0.3 g of NaH (80% strength) in 50 ml of dimethyl sulfoxide (DMSO) at 25°, and the mixture is stirred for 4 hours. Customary working-up and purification by column chromatography (ethyl acetate/methanol) give 2,2-dimethyl-4-(1-methyl-1,6-dihydro-6-oxo-3-pyridazinyl-amino)-6-cyano-3chromanol, m.p. 117°–119°.

The following are obtained analogously: from 3-amino-1-benzyl-1,6-dihydropyridazin-6-one- and "IIa":
2,2-dimethyl-4-(1-benzyl-1,6-dihydro-6-oxo-3-pyridazinyl-amino)-6-cyano-3-chromanol, m.p. 233°–236°;
from 3-N-methylamino-1-methyl-1,6-dihydropyridazin-6-one and "IIa":
2,2-dimethyl-4-(1-methyl-1,6-dihydro-6-oxo-3-pyridazinyl-N-methyl-amino)-6-cyano-3-chromanol, m.p. 242°–244°;
from 3-amino-1-isopropyl-1,6-dihydropyridazin-6-one and "IIa":
2,2-dimethyl-4-(1-isopropyl-1,6-dihydro-6-oxo-3-pyridazinyl-amino)-6-cyano-3-chromanol, m.p. 223°–225°;
from 3-amino-1-ethyl-1,6-dihydropyridazin-6-one and "IIa":
2,2-dimethyl 4-(1 ethyl-1,6-dihydro-6-oxo-3-pyridazinyl-amino)-6-cyano-3-chromanol, m.p. 225°–228°;
from 3-amino-1-methyl-1,6-dihydropyridazin-6-one and 2,2,3-trimethyl-3,4-epoxy-6-cyano-chroman:
2,2,3 trimethyl-4-(1-methyl-1,6-dihydro-6-oxo-3-pyridazinyl-amino)-6-cyano-3-chromanol, m.p. 258°–260°;
from 3-amino-1-methyl-1,6-dihydropyridazin-6-one and 2,2-dimethyl-(3S,4S)-epoxy-6-cyano-chroman:
2,2-dimethyl-(4R)-(1-methyl-1,6-dihydro-6-oxo-3-pyridazinyl-amino)-6-cyano-(3S)-chromanol, m.p. 177°–180°
from 4-amino-1-methyl-1,2-dihydropyridin-2-one and 2,2-dimethyl-(3S,4S)-epoxy-6-cyano-chroman:
2,2-dimethyl-(4R)-(1-methyl-1,2-dihydro-2-oxo-4-pyridyl-amino)-6-cyano-(3S)-chromanol, m.p. 283°–285° C.

EXAMPLE 2

A mixture of 1.1 g of 1-amino-1,2-dihydropyridin-2-one and 3.1 g of 2,2,3-trimethyl-3,4-epoxy-6-cyano-chroman is heated to the melting point and stirred at this temperature for 8 hours. The residue is purified by column chromatography (dichloromethane/ethyl acetate; silica gel). 2,2,3-Trimethyl-4-(1,2-dihydro-2-oxo-1-pyridyl-amino)-6-cyano-3-chromanol, m.p. 184°–187°, is obtained.

The following is obtained analogously: from 1-amino-1,2-dihydro-pyridin-2-one and "IIa":
2,2-dimethyl-4-(1,2-dihydro-2-oxo-1-pyridyl-amino)-6-cyano-3-chromanol, m.p. 202°–204°.

EXAMPLE 3

0.5 ml of triethylamine is added to a solution of 1.1 g of 3-amino-1,6-dihydropyridin-6-one and 2.0 g of "IIa" in 50 ml of ethanol, and the mixture is boiled for 2 hours. Customary working-up gives 2,2-dimethyl-4-(1,6-dihydro-6-oxo-3-pyridyl-amino)- 6-cyano-3-chromanol, m.p. 285°–287°.

The following is obtained analogously from 3-amino-1,2-dihydropyridin-2-one and "IIa":
2,2-dimethyl-4-(1,2-dihydro-2-oxo-3-pyridyl-amino)-6-cyano-3-chromanol, m.p. 278°–280°.

EXAMPLE 4

2,2-dimethyl-4-(1,4-dihydro-4-oxo-3-pyridyl-amino)-6-cyano-3-chromanol, hydrochloride, m.p. 268°–270° is obtained analogously to Example 3 from the HCl salt of 3-amino-1,4-dihydro-pyridin-4-one and "IIa".

EXAMPLE 5

A mixture of 1.1 g of 3-N-methylamino-1-methyl-1,6-dihydropyridazin-6-one, 2.0 g of "IIa" and 0.3 g of NaH (80% strength) is stirred in 50 ml of DMSO at 20° for 6 hours and worked up in the customary manner. This gives 2,2-dimethyl-4-(1-methyl-1,6-dihydro-6-oxo-3-pyridazinyl-N-methyl-amino)-6-cyano-3-chromene, m.p. 134°–136°.

The following is obtained analogously from 4-amino-1-methyl-1,2-dihydropyridin-2-one and "IIa":
2,2-dimethyl-4-(1-methyl-1,2-dihydro-2-oxo-4-pyridyl-amino)-6-cyano-3-chromene, m.p. 200°–202°.

EXAMPLE 6

2.0 g of 2,2-dimethyl-4-(1-methyl-1,6-dihydro-6-oxo-3-pyridazinyl-amino)-6-cyano-3-chromanol are boiled in 20 ml of acetic anhydride for 2 hours. Customary working-up gives 2,2-dimethyl-3-acetoxy-4-(1-methyl-1,6-dihydro-6-oxo-3-pyridazinyl-amino)-6-cyano-3-chromene, m.p. 110°–112°.

The examples below relate to pharmaceutical preparations which contain compounds of the formula I or their physiologically acceptable salts:

EXAMPLE A

Tablets

A mixture of 1 g of 2,2-dimethyl-4-(1-methyl-1,6-dihydro-6-oxo-3-pyridazinyl-amino)-6-cyano-3-chromanol, 4 kg of lactose, 1.2 kg of potato starch, 0.2 g of talc and 0.1 kg of magnesium stearate is pressed to give tablets in a customary manner, in such a way that each tablet contains 0.1 mg of active compound

EXAMPLE B

Coated tablets

Tablets are pressed analogously to Example A, and are subsequently coated in a customary manner with a coating of sucrose, potato starch, talc, tragacanth and colorant.

EXAMPLE C

Capsules

Hard gelatin capsules are filled in a customary manner using 1 kg of 2,2,3-trimethyl-4-(1-methyl-1,6-dihydro-6-oxo-3-pyridazinyl-amino)-6-cyano-3-chromanol so that each capsule contains 0.5 mg of active compound.

EXAMPLE D

Ampoules

A solution of 10 g of 2,2-dimethyl-4-(1-methyl-1,6-dihydro-6-oxo-3-pyridazinyl-amino)-6-cyano-3-with double-distilled water, sterile filtered, the solution is filled into ampoules, and the ampoules are sealed in a sterile manner. Each ampoule contains 0.1 mg of active compound.

Analogously, tablets, coated tablets, capsules or ampoules are obtainable which contain one or more of the other active compounds of the formula I and/or their physiologically acceptable salts.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A chroman compound of Formula I

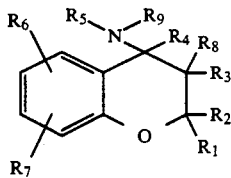

wherein $R^1$ is A, $R^2$, $R^8$ and $R^9$ are each independently H or A, or $R^1$ and $R^2$ together are alkylene having 3-6 C atoms, $R^3$ is H, OH, OA or $OR^{10}$, $R^4$ is H, or $R^3$ and $R^4$ together are a bond, $R^5$ is a pyridazinyl, oxodihydropyridazinyl radical which is unsubstituted, monosubstituted or disubstituted by A, F, Cl, Br, I, OH, OA, $OR^{10}$, SH, $NO_2$, $HN_2$, $R^{10}NH$, HOOC and/or AOOC, $R^6$ and $R^7$ are each independently H, A, HO, AO, CHO, ACO, ACS, HOOC, AOOC, AO—CS, ACOO, A—CS—O, HO—$C_nH_{2n}$, HS—$C_nH_{2n}$, $NO_2$, $HN_2$, NHA, $NA_2$, CN, F, Cl, Br, I, $CF_3$, ASO, $ASO_2$, AO—SO, —AO—$SO_2$, $R^{10}NH$, AO—CO—NH, $H_2HSO$, HANSO, $A_2NSO$, $H_2NSO_2$, $HANSO_2$, $A_2NSO_2$, $H_2NCO$, HANCO, $A_2NCO$, $H_2NCS$, HANCS, $A_2NCS$, ASONH, $ASO_2NH$, AOSONH, $AOSO_2NH$, ACO—$C_nH_{2n}$, nitro—$C_nH_{2n}$, cyano—$C_nH_{2n}$, A—C(=NOH) or A—C(=$NNH_2$), A is alkyl having 1-6 C atoms R is alkanoyl having 1-8 C atoms or aroyl having 7-11 C atoms and n is 1-6, or a physiologically acceptable salt thereof.

2.
   (a) 2,2-Dimethyl-4-(l-methyl-1,6-dihydro-6-oxo-3-pyridazinyl-amino)-6-cyano-3-chromanol;
   (b) trans-3,4-dihydro-4-(1,6-dihydro-1-methyl-6-oxo-3-pyridazinyl-amino)-2,2,3-trimethyl-6-cyano-3-chromanol;
   (c) (4R,3S)-2,2-dimethyl-4-(1-methyl-1,6-dihydro-6-oxo-3-pyridazinyl-amino)-6-cyano -3-chromanol; or
   (d) 2,2-dimethyl-4-[N-(1-methyl-6-oxo-3-pyridazinyl)-N-methylamino]-6-cyano-3-chromanol, each a compound of claim 1.

3. A pharmaceutical composition comprising at least one compound of the formula I and/or a physiologically acceptable salt thereof, and a pharmaceutically acceptable carrier.

4. A method for the treatment of decompensated cardiac insufficiency, angina pectoris, cardiac arrhythmia, peripheral or cerebral vessel disorders, asthma, urinary incontinence or alopecia in a host, comprising administering to said host an effective amount of a compound of claim 1 or a physiologically acceptable salt thereof.

5. A method of achieving a vasodilatory effect in a host, comprising administering an effective amount of a compound of claim 1 or a physiologically acceptable salt thereof.

* * * * *